United States Patent [19]

Harnden et al.

[11] 4,405,794

[45] Sep. 20, 1983

[54] PREPARATION OF 2-OXAZOLIDINONE AND ETHYLENEUREA

[75] Inventors: Robert M. Harnden, Russellville, Ark.; Daniel W. Baugh, Jr., Lake Jackson, Tex.

[73] Assignee: The Dow Chemical Company, Midland, Mich.

[21] Appl. No.: 332,290

[22] Filed: Dec. 18, 1981

[51] Int. Cl.³ .................. C07D 263/22; C07D 233/30
[52] U.S. Cl. ...................................... 548/229; 548/317
[58] Field of Search ................................ 548/229, 317

[56] References Cited

U.S. PATENT DOCUMENTS

| | | | |
|---|---|---|---|
| 2,399,118 | 4/1946 | Homeyer | 548/229 |
| 2,430,874 | 11/1947 | Hale | 548/317 |
| 2,436,311 | 2/1948 | Larson et al. | 548/317 |
| 2,437,388 | 3/1948 | Homeyer | 548/229 |
| 2,437,389 | 3/1948 | Homeyer | 548/229 |
| 2,437,390 | 3/1948 | Homeyer | 548/229 |
| 2,497,308 | 2/1950 | Larson | 548/317 |
| 2,517,750 | 8/1950 | Wilson | 548/317 |
| 2,526,757 | 10/1950 | Larson et al. | 548/317 |
| 2,755,286 | 7/1956 | Bell et al. | 548/229 |
| 2,842,523 | 7/1958 | Tousignant et al. | 560/165 |
| 2,892,843 | 6/1959 | Levine | 548/317 |
| 2,977,370 | 3/1961 | Oken | 548/229 |
| 3,133,932 | 5/1964 | Horn et al. | 548/229 |
| 3,179,667 | 4/1965 | Walles | 548/229 |
| 3,215,701 | 11/1965 | Pomot | 548/229 |
| 3,687,965 | 8/1972 | Fauran et al. | 548/229 |
| 4,063,021 | 12/1977 | Cipriani et al. | 548/317 |
| 4,209,628 | 6/1980 | Ikeda et al. | 548/229 |
| 4,250,318 | 2/1981 | Dostert et al. | 548/229 |

Primary Examiner—Nicholas S. Rizzo
Assistant Examiner—S. A. Gibson
Attorney, Agent, or Firm—A. J. Young

[57] ABSTRACT

The present invention provides a method for reacting urea and beta-hydroxyethylcarbamate to make 2-oxazolidinone and ethyleneurea in a good yield and high selectivity, whereby the reaction method can be controlled to provide either the 2-oxazolidinone or the ethyleneurea as the major reaction product.

8 Claims, No Drawings

PREPARATION OF 2-OXAZOLIDINONE AND ETHYLENEUREA

BACKGROUND OF THE INVENTION

This invention relates to the preparation of 2-oxazolidinone and ethyleneurea. More particularly, this invention relates to the preparation of 2-oxazolidinone and ethyleneurea by reacting urea with beta-hydroxyethylcarbamate.

Known methods of preparing 2-oxazolidinone include (a) the reaction of a beta-amino alcohol and an alkyl carbonate; (b) the thermal decomposition of N(-2-hydroxyalkyl)-2-hydroxyalkyl carbonates or of 2-aminoethyl carbamates; (c) the reaction of epoxides with organic isocyanates or their dimers; or (d) the reaction of carbon dioxide with ethyleneimine. In addition, known methods of preparing ethyleneurea include (a) heating ethylenediamine with diethyl carbonate; (b) warming an aqueous solution of ethylenethiourea with freshly precipitated mercuric oxide; (c) distilling an aqueous solution of ethyleneguanidine under reduced pressure; or (d) reacting urea with a compound $XCH_2CH_2Y$, wherein X or Y is —OH, —$NH_2$, —$OCO_2$, or a halogen, or wherein X and Y are oxygen.

Both 2-oxazolidinone and ethyleneurea are important intermediates for making other products of special value. However, a method for making both compounds in the same reaction where the reaction can be controlled to selectively provide either as the major reaction product is not known.

SUMMARY

In general, the present invention provides a process for the preparation of 2-oxazolidinone and ethyleneurea, which comprises the step of reacting urea with beta-hydroxyethylcarbamate to form 2-oxazolidinone and ethyleneurea. The term "ethyleneurea" as herein defined means N,N'-ethyleneurea.

It is an object of this invention to provide a process for the preparation of 2-oxazolidinone and ethyleneurea. It is a further object of this invention to provide a process that can be controlled to selectively produce predominantly either 2-oxazolidinone or ethyleneurea. It is a further object of this invention to provide a process therefor which is highly selective with respect to both of the desired products, which is further selective to either product, and which produces a minimum of undesirable byproducts. Other objects of the present invention will be apparent to those skilled in the art from the more detailed description which follows.

DESCRIPTION OF THE PREFERRED EMBODIMENTS

The following description illustrates the manner in which the principles of the present invention are applied, but is not to be construed as in any sense limiting the scope of the invention.

More specifically, the present invention comprises the process of reacting urea and beta-hydroxyethylcarbamate at a temperature between about 155° C. and about 235° C. The mole ratio of urea to beta-hydroxyethylcarbamate is beneficially between about 0.75 to one and about two to one, and, preferably, between about 1.25 to one and about 1.5 to one.

If it is desired to maximize the yield of 2-oxazolidinone, the reaction may beneficially be carried out at a temperature between about 185° C. and about 195° C. If it is desired to maximize the yield of ethyleneurea, the reaction may beneficially be carried out at a temperature between about 210° C. and about 225° C. In the case of maximizing ethyleneurea, it is especially useful to stage the addition of urea, although such stagewise addition will reduce the undesirable formation of hydroxyethylethyleneurea in either case. When stagewise addition of urea is utilized, the initial mole ratio of urea to beta-hydroxyethyl carbamate at the beginning of the reaction is preferably about one to one, with the remaining urea added during the course of the reaction. Such stagewise addition may be either incremental or continuous.

The reaction between urea and beta-hydroxyethylcarbamate may be continued for a period of time between about a half hour and about four hours. If the reaction mixture is held longer than about four hours or the reaction carried out above about 225° C., selectivity may be decreased due to the formation of polymeric byproducts. In general, lower temperatures and shorter reaction times are used when 2-oxazolidinone is the desired product. However, reaction temperatures below about 185° C. result in a very slow reaction.

The invention will now be illustrated by means of the following examples.

EXAMPLE 1

Twenty-one grams (200 millimoles) of crystalline beta-hydroxyethylcarbamate was weighed into a three-necked round-bottomed flask, together with fifteen grams (250 millimoles) of prilled urea, thereby providing a molar ratio of urea to beta-hydroxyethylcarbamate of 1.25 to one. The flask was fitted with a water-cooled condenser, stirring bar, and thermometer. The reaction mass was then heated to a temperature of 185° C., with continuous stirring. The mixture was sampled periodically, and the samples were analyzed by gas-solid chromatography to monitor the progress of the reaction. After a period of two hours, the yield of 2-oxazolidinone had maximized. Identifiable reactants and products at this point comprised sixty-six percent 2-oxazolidinone, twenty-two percent ethyleneurea, nine percent unreacted beta-hydroxyethylcarbamate, and three percent (mono)ethylene glycol on a weight basis. The reaction mass was heated with stirring for an additional thirty minutes, whereupon the composition of the mixture was found to be sixty-four percent 2-oxazolidinone, twenty-six percent ethyleneurea, four percent unreacted beta-hydroxyethylcarbamate, and six percent (mono)ethylene glycol. The following calculated results are based on the two-hour sample: ninety-seven percent accountability, ninety-three percent conversion of beta-hydroxyethylcarbamate, sixty-four percent yield of and selectivity to 2-oxazolidinone, twenty-six percent yield of and selectivity to ethyleneurea, and five percent yield of and selectivity to mono(ethylene) glycol.

EXAMPLE 2

Urea and beta-hydroxyethylcarbamate were added to a reaction flask as in Example 1, with the initial mole ratio of urea to beta-hydroxyethylcarbamate being one to one. The reagents were heated to 225° C. with continuous stirring. After fifteen minutes at 225° C., an additional increment of urea was added to the flask, whereby the molar ratio of total urea charged to total beta-hydroxyethylcarbamate charged was increased to 1.17 to one. Two further incremental additions, at fifteen-minute intervals, brought the mole ratio of total urea charged to total beta-hydroxyethylcarbamate charged to 1.33 to one and 1.50 to one, respectively. The reaction mixture was sampled and analyzed periodically, as in Example 1, and the reaction was terminated by cooling the reaction flask after a period of two and one-half hours. On analysis, the composition of the reaction-product mixture was found to comprise one percent 2-oxazolidinone, ninety-two percent ethyleneurea, and seven percent hydroxyethylethyleneurea, with a ninety-percent accountability. The components unaccounted for include polymeric ureas. The following calculated results are based on the foregoing data: one-hundred percent conversion of beta-hydroxyethylcarbamate, eighty-one percent yield of and selectivity to ethyleneurea, and eight percent yield of and selectivity to hydroxyethylethyleneurea.

While certain representative embodiments and details have been shown for the purpose of illustrating the present invention, it will be apparent to those skilled in the art that various changes and modifications can be made therein without departing from the spirit and scope of the invention.

What is claimed is:

1. A process for making 2-oxazolidinone and ethyleneurea, which comprises the step of reacting urea with beta-hydroxyethylcarbamate at elevated temperatures.

2. The process of claim 1, wherein the urea and beta-hydroxyethylcarbamate are reacted at a temperature between about 155° C. and about 235° C.

3. The process of claim 2, wherein the mole ratio of urea to beta-hydroxyethylcarbamate is between about 0.75 to one and about two to one.

4. The process of claim 3, wherein the mole ratio of urea to beta-hydroxyethylcarbamate is between about 1.25 to one and about 1.5 to one.

5. The process of claim 4, wherein the reaction temperature is between about 185° C. and about 195° C.

6. The process of claim 4, wherein the reaction temperature is between about 210° C. and about 225° C.

7. The process of claim 6, wherein the urea is added in stages.

8. The process of claim 5, wherein the urea is added in stages.

* * * * *